US009470514B2

United States Patent
Liu et al.

(10) Patent No.: US 9,470,514 B2
(45) Date of Patent: Oct. 18, 2016

(54) SYSTEM AND METHOD FOR USING LASER SCAN MICROMETER TO MEASURE SURFACE CHANGES ON NON-CONCAVE SURFACES

(71) Applicant: Southwest Research Institute, San Antonio, TX (US)

(72) Inventors: Eric Liu, Leon Valley, TX (US); Sean C. Mitchem, Helotes, TX (US); Kerry J. McCubbin, Helotes, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 14/620,020

(22) Filed: Feb. 11, 2015

(65) Prior Publication Data

US 2016/0231105 A1 Aug. 11, 2016

(51) Int. Cl.
*G06K 9/00* (2006.01)
*G01B 11/24* (2006.01)
*G01N 21/89* (2006.01)

(52) U.S. Cl.
CPC ....... *G01B 11/2433* (2013.01); *G01N 21/8901* (2013.01); *G06K 9/00* (2013.01)

(58) Field of Classification Search
CPC ............... G01N 21/8422; G01N 15/1475; G01N 21/9515; G01N 2035/0493; G01N 35/0099; G02B 21/088; G02B 21/006; G02B 26/10; A61M 16/0683; B21B 3/00; Y10S 435/967; Y10T 137/0324; G01B 11/255; G01B 15/02; G01B 11/002; G01B 11/005; G01B 11/245; G07D 7/20; A61L 2300/45; A61F 2/0077; A61F 2250/0067; G01S 7/4817; G01S 17/06; G01S 17/08; G01S 17/66; G01S 17/933; A61B 5/04; A61B 8/565; A61B 8/582; G06T 7/0057; G06K 9/00; B07C 3/00; G01R 31/2656; H05K 13/08; H01J 37/28
USPC ........ 382/141, 286, 291; 356/601, 608, 432, 356/630, 614, 634, 625
See application file for complete search history.

(56) References Cited

U.S. PATENT DOCUMENTS

| | | | | |
|---|---|---|---|---|
| 3,601,492 A | * | 8/1971 | Reichard ............ | G01B 11/0675 356/504 |
| 5,142,955 A | * | 9/1992 | Hale ................... | B23D 59/008 144/356 |
| 5,619,587 A | * | 4/1997 | Willoughby, Jr. ...... | B21C 51/00 356/630 |
| 5,774,220 A | * | 6/1998 | Wienecke ............ | G01B 11/002 250/559.23 |

(Continued)

*Primary Examiner* — Vu Le
*Assistant Examiner* — Aklilu Woldemariam
(74) *Attorney, Agent, or Firm* — Livingston Law Firm

(57) ABSTRACT

A method of comparing surface profiles of an object, the object being rotatable on an axis, such that the object has a longitudinal dimension and an axial dimension. The object is incrementally scanned with a laser scan micrometer, first in a pre-test scan procedure and then in a post-test scan procedure. The two scan procedures are performed in the same manner, by using the laser scan micrometer to scan the object in a longitudinal direction, rotating the object, re-scanning the object, measuring the scan length thereby obtaining a longitudinal height value, and repeating the preceding steps for a number of incremental rotations thereby obtaining one longitudinal height profile. This process is repeated by incrementally moving the object in an axial direction and acquiring additional longitudinal height profiles, thereby acquiring a set of longitudinal height profiles. The pre-test and post-test sets of profiles are then aligned and compared.

18 Claims, 8 Drawing Sheets

(56) References Cited

U.S. PATENT DOCUMENTS

| | | | | |
|---|---|---|---|---|
| 5,838,587 A | * | 11/1998 | Maisotsenko | F15D 1/02 137/2 |
| 6,480,285 B1 | * | 11/2002 | Hill | G01B 9/04 356/492 |
| 5,838,587 A | * | 11/1998 | Maisotsenko | F15D 1/02 137/2 |
| 6,480,285 B1 | * | 11/2002 | Hill | G01B 9/04 356/492 |
| 7,161,688 B1 | * | 1/2007 | Bonner | G01B 11/04 356/625 |
| 2003/0060998 A1 | * | 3/2003 | Millgard | B64F 1/305 702/127 |
| 2005/0288891 A1 | * | 12/2005 | Masuyama | E01C 23/01 702/167 |
| 2008/0218850 A1 | * | 9/2008 | Power | G02B 21/088 359/385 |
| 2009/0290204 A1 | * | 11/2009 | Hirata | G01S 7/4814 359/199.1 |
| 2010/0091300 A1 | * | 4/2010 | Thomaschewski | G01S 17/89 356/601 |
| 2011/0039709 A1 | * | 2/2011 | Lips | G01N 35/0099 506/7 |
| 2015/0008346 A1 | * | 1/2015 | Mantyla | D21F 7/06 250/559.01 |

* cited by examiner

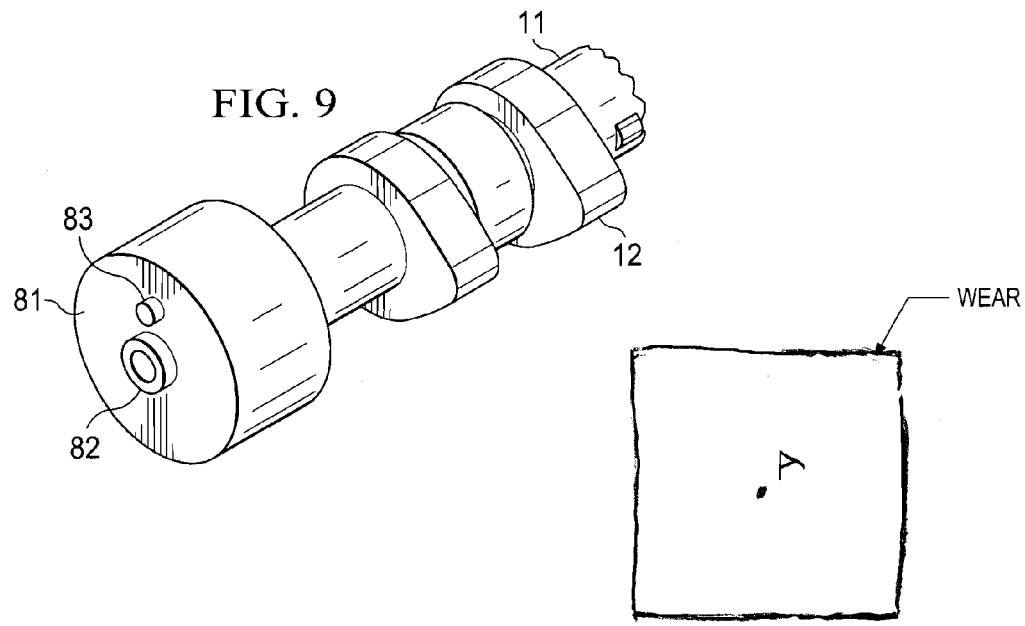
FIG. 9
FIG. 11
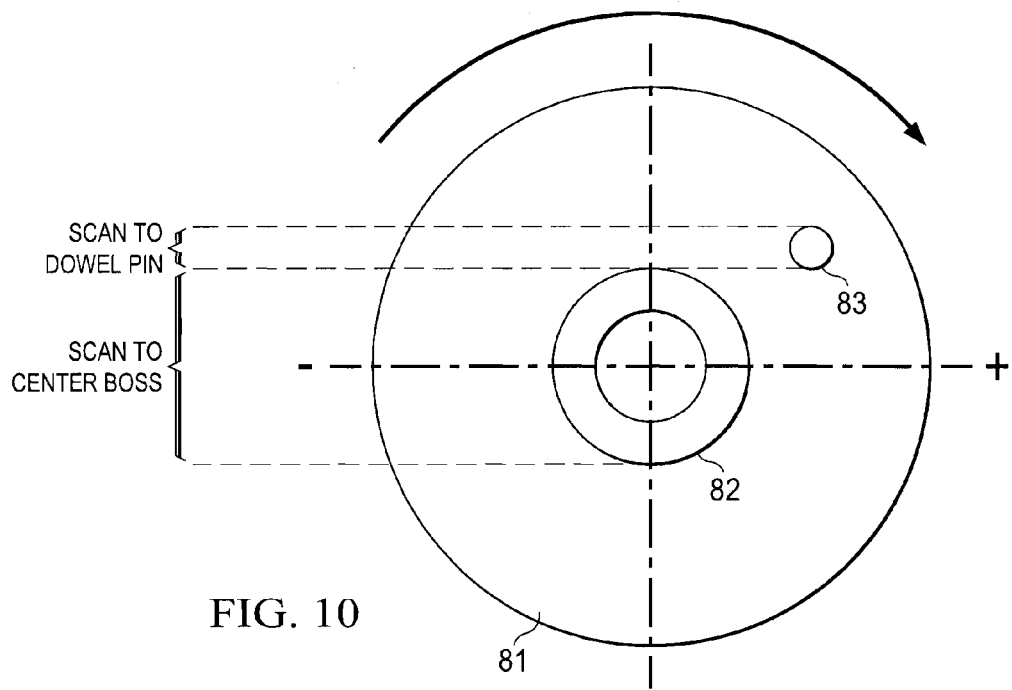
FIG. 10

US 9,470,514 B2

SYSTEM AND METHOD FOR USING LASER SCAN MICROMETER TO MEASURE SURFACE CHANGES ON NON-CONCAVE SURFACES

TECHNICAL FIELD OF THE INVENTION

This invention relates to using a laser scan micrometer to measure wear (or other gain or loss of material) on surfaces of machine parts and other discrete objects.

BACKGROUND OF THE INVENTION

In materials science, "wear" can be defined as erosion or displacement of material from its original position on a solid surface performed by the action of another surface. Thus, wear is related to mechanical interactions between surfaces, and more specifically, to the removal or deformation of material on a surface as a result of mechanical action of an opposing surface.

In the field of surface engineering, many different test methodologies have been developed in efforts to evaluate wear during the working life of machine components. Specific test methods exist for different types and shapes of components to determine an amount of material removal during a specified time period under well-defined conditions.

The evaluation of wear on a used specimen typically involves measuring changes between the mass and/or surface topography of the specimen before use and the same specimen after use. In a testing environment, these parts can be referred to as pre-test and post-test specimens, respectively.

Conventional topographic wear measurement methods use contact profilometry with a stylus profilometer to obtain surface profiles of pre-test and post-test specimens. The pre-test and post-test surface profiles are obtained from the same area on the test specimen and are overlaid using common features that have not experienced wear or other topographic changes.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIG. 9 is a perspective view of the front face of a conventional camshaft.

FIG. 10 is a front view of the front face of a conventional camshaft, and illustrates a rotational alignment process.

FIG. 11 illustrates an example of a cross-sectional profile of a test object other than a cam, with which the method may be used.

DETAILED DESCRIPTION OF THE INVENTION

The following description is directed to a method that measures changes in surface topography of a test specimen. Although the method can be used to detect either loss or gain of surface material, the method is especially useful for measuring wear (loss of material).

The method is useful for machine parts and other "discrete" objects that can be handled and placed in the laser scan measurement system described below. The test objects are three-dimensional objects having a cross-sectional profile with no concavities. Examples of such cross-sectional profiles are rectangular and rounded profiles, with the latter including only convex curved surfaces.

For purposes of example herein, the test object is a cam and remains mounted on its camshaft during measurements. A cam is generally understood to have a rounded cross-sectional profile with one or more convex features (lobes). Because the cam is measured by being rotated on an axis, it will be considered to have an axial dimension, as well as a longitudinal dimension orthogonal to the axial dimension. The cross-sectional profile is in a third plane normal to the axial dimension. The method can be used to measure wear on the cam surface in the axial and longitudinal dimensions.

Figure 1:
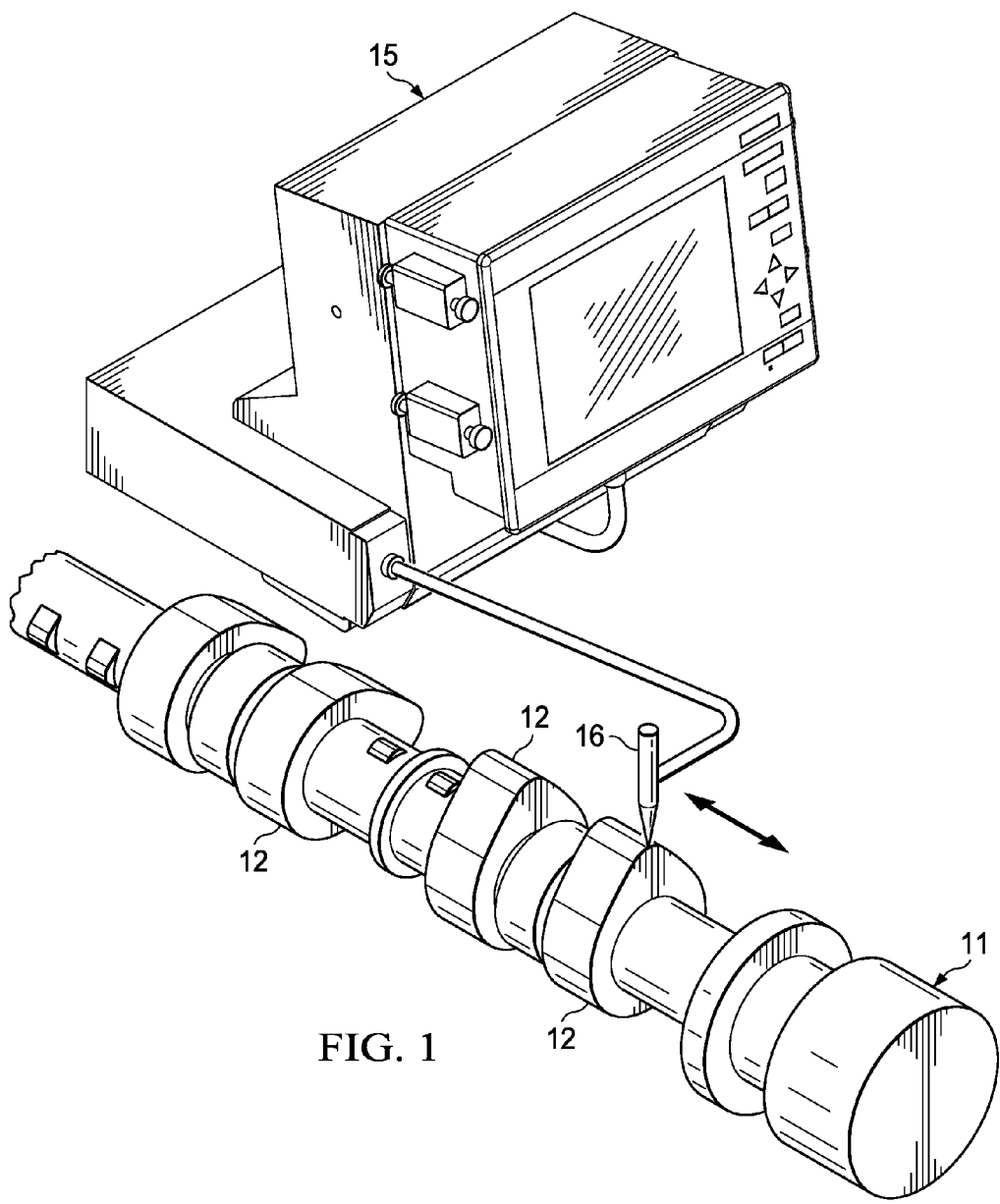
FIG. 1 illustrates how an axial profile trace is conventionally obtained, using a profilometer.

FIG. 1 illustrates how an axial profile trace is conventionally obtained, using a profilometer. The test objects are automotive cams 12, which are tested while remaining installed on their camshaft 11.

The profilometer 15 is being used to measure wear of one cam 12. The profilometer's stylus 16 is positioned against (in contact with) the cam surface. While the cam 12 is stationary, the stylus 16 is moved across the cam's surface in the cam's axial direction. This direction is indicated by the arrow.

The profile trace is referred to as an "axial profile" because the stylus 16 is moved in the same direction as the camshaft (axis) 11 that is used to rotate the cam 12. The cam 12 may then be rotated to obtain additional axial profile traces.

Figure 2:
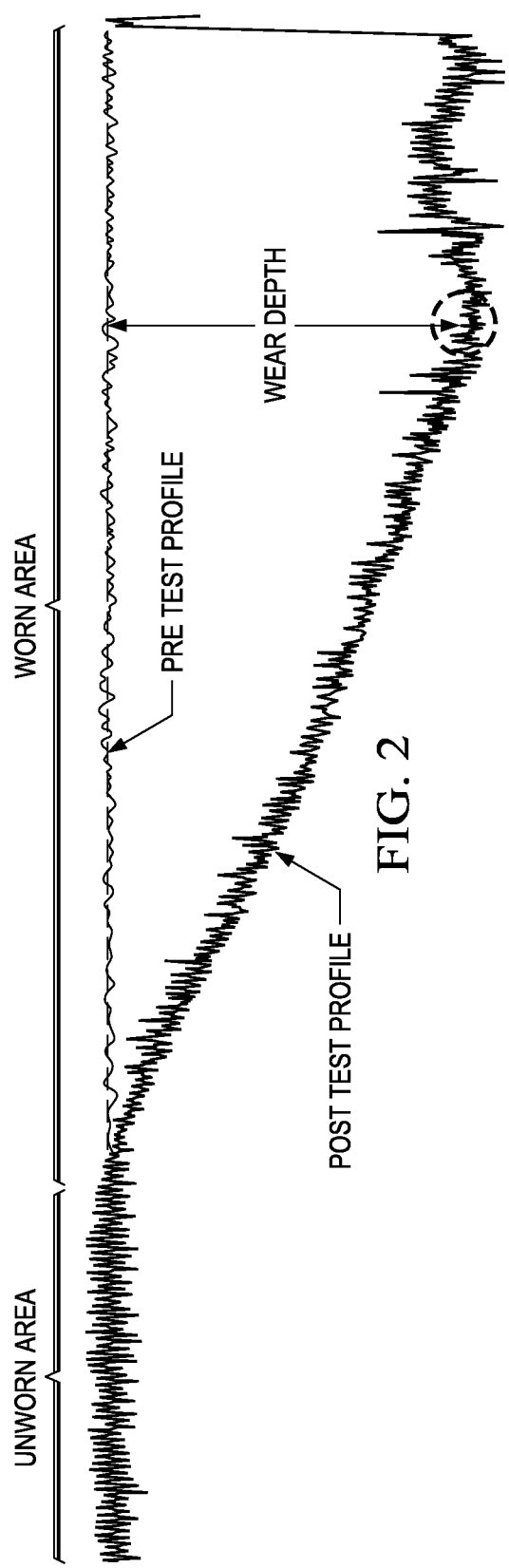
FIG. 2 illustrates an example of overlaying a pre-test and a post-test axial profile.

FIG. 2 illustrates an example of overlaying a pre-test and a post-test axial profile. The pre-test and post-test profile traces have been obtained in the manner illustrated in FIG. 1.

A comparison of the two axial profiles is used to determine wear. The pre-test profile is flat across the surface. Surface damage caused by wear is clearly observed on the post-test profile. The wear may be evaluated as a depth measurement of the vertical deviation of the post-test profile from the pre-test profile.

In the example of FIG. 2, an unworn edge of the cam, shown on the left side of the trace, was used as a reference for overlaying the traces. In other words, unworn topographic features (edges of the cam) may be used as axial references to correctly position one profile against the other in space.

A feature of the invention is that surface profiles are acquired using a laser scan micrometer. Unlike a stylus profilometer, a laser scan micrometer is a non-contact measurement instrument. As explained below, rather than having its surface traced axially as in FIG. 1, the test object is scanned longitudinally with a laser beam. The test object blocks the laser beam and thereby casts a shadow. The laser scan micrometer measures the length of the shadow, which represents a measurement of the object in the direction of the scan.

Figure 3:
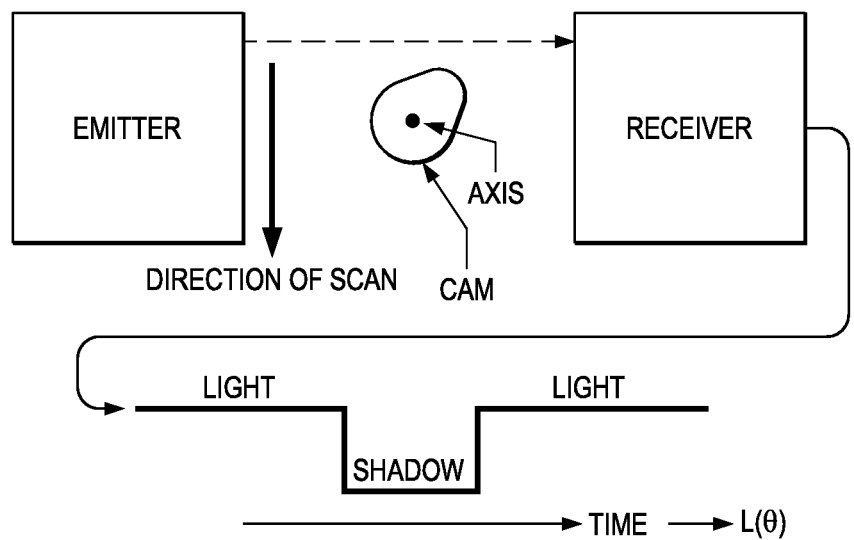
FIGS. 3 and 4 illustrate two types of laser scan micrometers.
Figure 4:
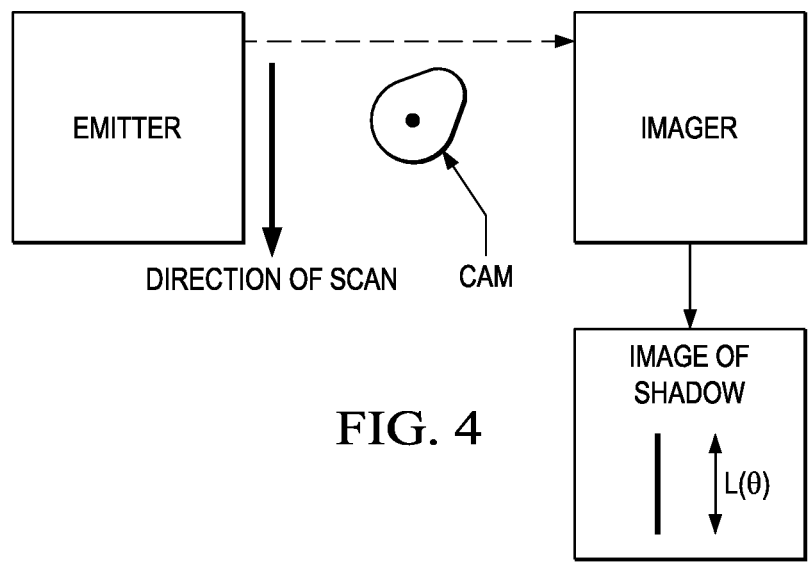

FIGS. 3 and 4 illustrate two types of laser scan micrometers. Either is suitable for implementation of the method described herein. Both directly or indirectly measure the length of a shadow cast by the test object.

In FIG. 3, the laser micrometer is a "time of interruption" laser micrometer. The laser micrometer has a laser emitter that emits a laser beam that scans across a measuring range. An object placed in the measuring field interrupts the laser beam and casts its shadow into a receiver. By measuring the time while the laser light is blocked, the length of the object in the longitudinal direction, hereinafter referred to as its "longitudinal height" can be computed.

In FIG. 4, the laser micrometer is a "length of shadow" laser micrometer. Like the micrometer of FIG. 3, the laser micrometer has a laser emitter, and an object placed in the measuring field interrupts the laser beam. However, with the micrometer of FIG. 4, the shadow is cast upon an imaging device. By measuring the shadow length on the received image, a longitudinal height of the object is measured.

Using either type of micrometer, one laser scan results in a measurement of a longitudinal height of the object at the object's present angular orientation and at one axial position of the object. A longitudinal height profile of the object can be obtained by scanning the object at different angular orientations, θ. Because the laser micrometer measures the length of a shadow cast from the object blocking a line of light, the same shadow will be measured if the object is rotated 180° around its axis. Therefore, it is only necessary to take measurements at small angular increments within a 180° range.

Figure 5:
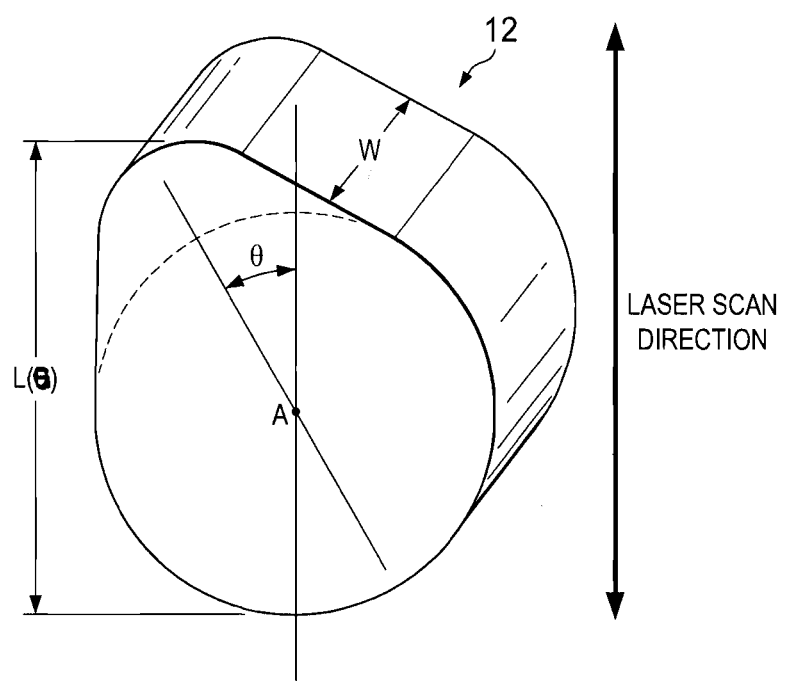
FIG. 5 illustrates a cam whose surface wear is to be measured.

FIG. 5 illustrates a cam 12 whose surface wear is to be measured. Cam 12 is to be rotated around an axis, A, normal to the cross-sectional profile. The cam's cross-sectional profile is shown, as well as an angular orientation, θ, and a height, L(θ), at that orientation. As a laser beam is scanned along the illustrated scan direction, the cam casts a shadow, whose length is measured and represents L(θ).

It be easily seen that if the cam is rotated, the value of L(θ) varies. At θ=0, the value of L will be maximum, whereas at θ=+/−90, the value of L will be minimum.

Figure 6:
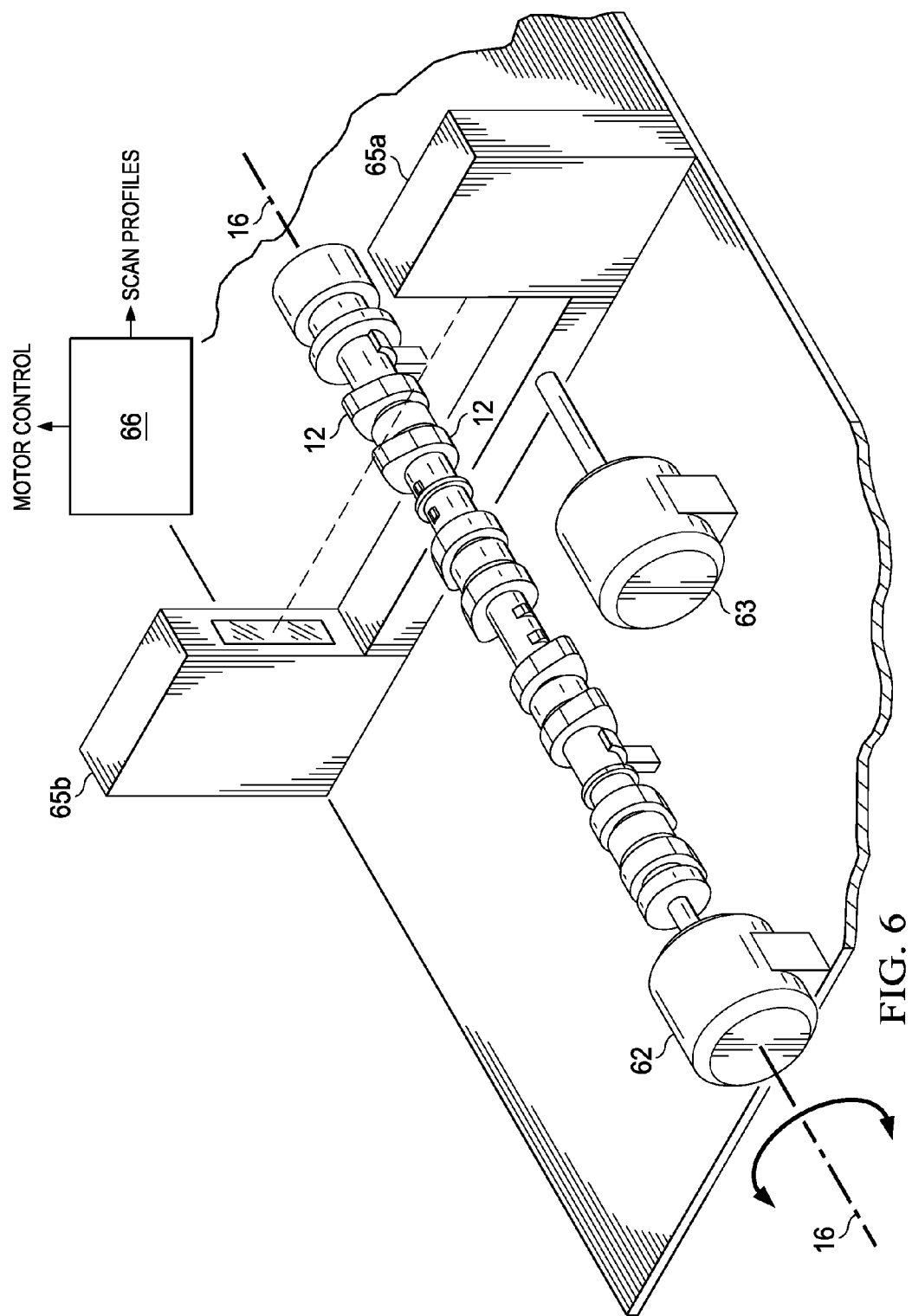
FIG. 6 illustrates a laser scan measurement system for obtaining surface profiles of a test object.

FIG. 6 illustrates a laser scan measurement system for obtaining surface profiles of a test object. Again, the test object is assumed to be a cam 12, but in general, the test object may have any cross-sectional profile with the surface of interest not having concave geometries.

A single test cam 12 mounted on an axis 61 is shown. Protrusions associated with cam 12, used for aligning profiles, are not explicitly shown, but may be included and are discussed below in connection with FIGS. 9 and 10.

A laser scan micrometer 65 has an emitter 65a and a receiver 65b. A laser beam travels from the emitter 65a to the receiver 65b. The laser scan direction is along the longitudinal dimension, L, of the cam. At a particular angular orientation, θ, of the cam, the shadow cast by the cam is detected and measured by receiver 65b. The length of the shadow represents a longitudinal measurement of the cam at that particular angular orientation.

A rotational stepper motor 62 is operable to rotate the axis 61 so that the cam 12 can be repositioned at different angular orientations. An axial stepper motor 63 is operable to shift a platform upon which the laser scan micrometer 65 is mounted. This allows the laser beam to be repositioned in the axial direction, that is, along the width, W, of the cam. Alternatively and equivalently, the cam or the axis could be axially repositioned. It is expected that suitable stepper motors can be implemented that are accurate to within +/−0.005 mm axially and +/−0.025 degrees angularly.

A control unit 66 has appropriate software and hardware for implementing the method described herein. Specifically, control unit 66 generates control signals to control the stepper motors 62 and 63. It receives and records laser measurement data outputted from laser scan micrometer 65. As explained below, control unit 66 may be further programmed to detect reference features and spatially align pre-test and post-test profiles. It may be further programmed to calculate and generate data representing profile differences.

Control unit 66 may also have the control hardware or software for controlling scanning by the laser scan micrometer 65. Alternatively, the laser scan micrometer 65 may be independently controlled, manually or automatically, to perform the scans described herein.

Figure 7A:
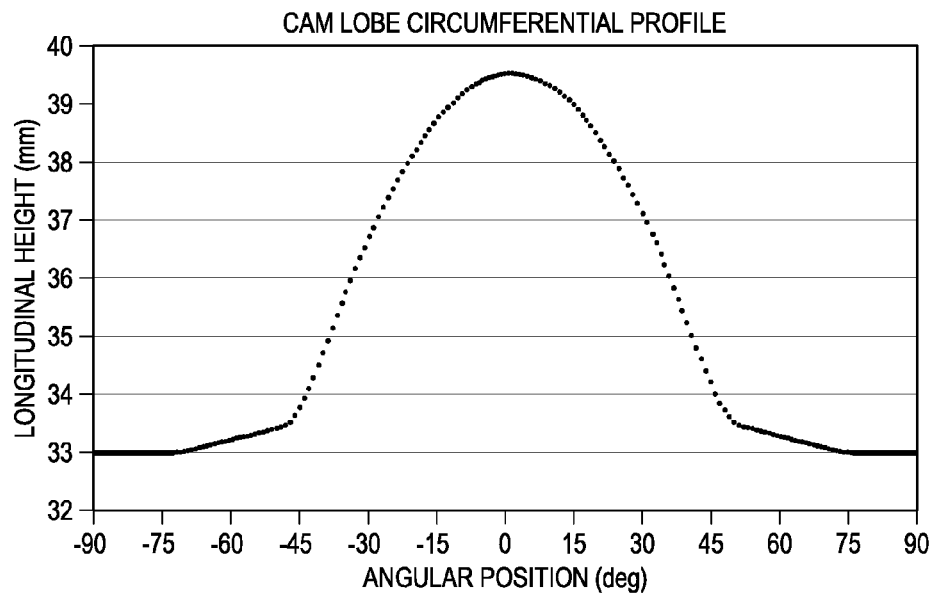
FIG. 7A illustrates a pre-test longitudinal height profile of a cam as acquired by the system of FIG. 6.

FIG. 7A illustrates a pre-test longitudinal height profile of cam 12 as acquired by the system of FIG. 6. Because the measurements are taken at increments while the object is rotated, this profile may also be referred to as "circumferential". This profile is obtained at a first axial position of the object. The height of the cam, L, was measured at different angular orientations, θ, for example, at 1° increments, for 180°.

Referring to both FIGS. 5 and 7A, it can be seen that as the cam rotates, its measured "length" changes due to its particular geometry. Other objects of various geometries will similarly display profiles representing their longitudinal heights.

Further referring to both FIGS. 5 and 6, the cam also has a width dimension, W. Using the system of FIG. 6, it is possible to obtain a set of circumferential profiles as the laser micrometer 65 is stepped axially across the cam's width.

Figure 7B:
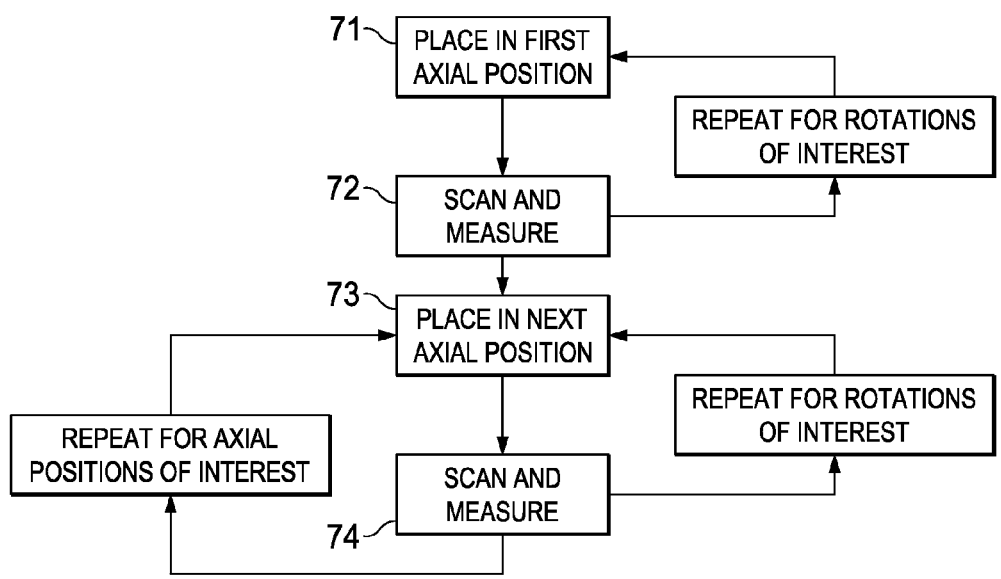
FIG. 7B illustrates the process of obtaining a set of longitudinal height profiles, using the system of FIG. 6.

FIG. 7B illustrates the process of obtaining a set of longitudinal height profiles, using the system of FIG. 6. The object is assumed to be mounted into the test system on an axis that allows it to be rotated as described above. The object can be mounted on an axis already associated with the object, such as the above-described cam on its camshaft. Otherwise, the object can be attached by some means to an axis of rotation. The axis of rotation can be placed through the object or attached at one or both two sides of the object. In an alternative embodiment, the object could be placed upon a vertical support and rotated, with the laser scan micrometer being reoriented accordingly.

In Step 71, the test object is positioned in a first axial and rotational position. The first axial position is typically near one end of the object. In Step 72, the object is scanned and a measurement recorded from its shadow. The object is then incrementally rotated around a rotational range of interest, which is typically 180 degrees, and a measurement is taken at each angular increment. The result is a longitudinal height profile, such as the profile of FIG. 7A.

In Step 73, the laser micrometer (or the test object) is moved to a next incremental axial position. In Step 74, the object is again scanned and a measurement recorded from its shadow. The object is then again incrementally rotated around the rotation range of interest, which is typically 180 degrees, and a measurement is taken at each angular increment. The result is another longitudinal height profile, like the profile of FIG. 7A but representing a different axial location on the test object.

The process of Step 73 is repeated for a number incremental axial positions, until the surface of interest has been scanned and measured. The result is a set of surface profiles, which may be compared to other surface profiles taken at different conditions of the test object.

Although this description is in terms of first acquiring a longitudinal height profile by stepping rotationally, and then acquiring additional longitudinal height profiles by stepping axially, the same method could equivalently be performed in reverse.

For testing, the test object is subjected to conditions of wear or use, and re-tested. For example, an automotive cam may be placed in an engine, which is operated under expected driving conditions. The cam is then again placed into the test system of FIG. 6 and a post-test profile obtained.

Figure 8:
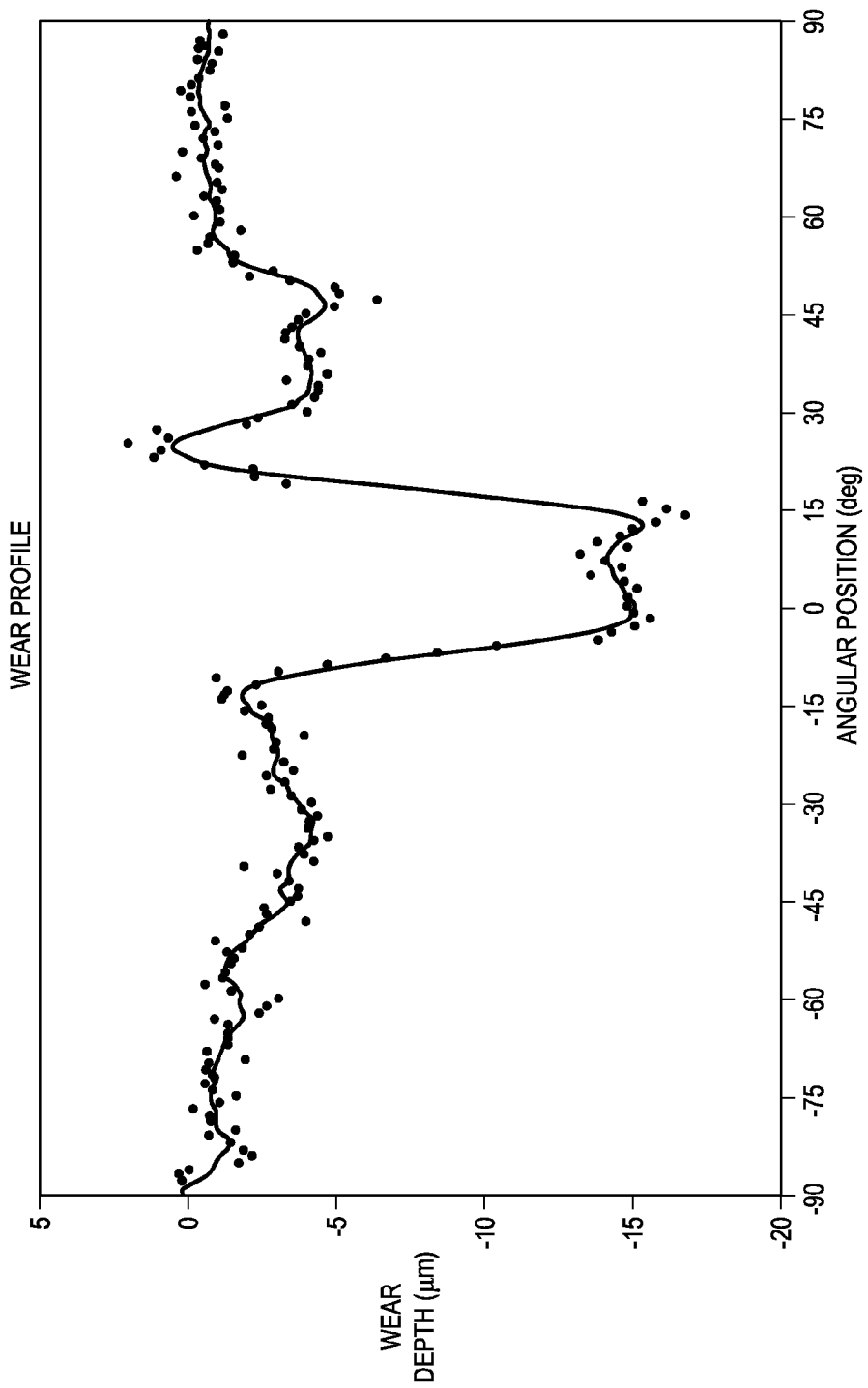
FIG. 8 illustrates an example of a "difference profile", which was obtained by overlaying a post-test profile against the pre-test profile of FIG. 7A.

FIG. 8 illustrates an example of a "difference profile", which was obtained by overlaying a post-test profile against the pre-test profile of FIG. 7A. At each angular position of the cam, the difference between the pre-test measurement and the post-test measurement is calculated and plotted. The difference profile indicates wear undergone by the cam over the course of the test duration.

As indicated above in connection with the profilometer method of FIG. 2, the overlaying of surface profiles requires some means for aligning the profiles. In FIG. 2, an unworn edge of a cam was used to overlay the two profiles. Unfortunately, unworn topographic features are not always available on a post-test specimen surface. This makes overlaying the pre-test and post-test profiles impossible using the profilometer method of FIG. 2.

For example, in the case of an automotive cam, the cam lobe may be in contact with a lifter face during its operation over the full width of the cam lobe. As a result, there is no surface on the cam lobe circumference that is not worn. If a conventional profilometer were used, a pre-test and post-test profile overlay with typical profilometer contact methods would be impossible using the method of FIG. 2.

However, using the laser scan micrometer system of FIG. 6, overlays may be achieved with non-changing reference features. One reference feature is used to determine an axial zero. Another pair of reference features is used to determine a rotational zero. As explained below, a single feature may double as both an axial and rotational reference feature.

FIGS. 9 and 10 are a perspective view and a front view, respectively, of the front face 81 of a conventional camshaft 11. A center boss 82 projects from face 81 around a center bore of the camshaft 11. A dowel pin 83 also projects from face 81. Significantly, the face 81, center boss 82, and dowel pin 83 each have smooth and machined surfaces.

These features on the face 81 of camshaft 11 provide the two non-changing reference features for index positioning of measurements and overlaying of surface profiles. "Non-changing" means that their physical state does not change between pre-test and post-test laser scanning. In general, this means that these features are not subjected to wear.

In the case of a cam mounted on a camshaft, the front face of the camshaft may be used for the axial zero because it is smooth and machined. The center boss 82 and dowel pin 83 are used for rotational reference. As illustrated in FIG. 10, for the rotational zero, an algorithm is used while scanning across the longitudinal axis of the center boss 82 and dowel pin 83. The rotational zero position is defined as the rotational position of the camshaft when the gap between the dowel pin 83 and the pilot boss 82 disappears. This is indicated by the point at which there is no measurable gap between their shadows according to the laser scan micrometer measurement.

When the test object is other than a cam mounted on a camshaft, and therefore not necessarily having a boss and/or dowel pin, other features may be used for overlaying pre-test and post-test profiles. A first non-changing feature is detected by the laser beam, and acts as an axial zero from which the axial position of the measurement line of the laser can be referenced. For rotational reference, two features protrude from the same face of the object. As the object is rotated, these features are detected by the laser, and provide a rotational zero as described above.

These reference features provide repeatable positioning of the laser scan micrometer measurement heads from the pre-test object to the post-test object. In other embodiments, a feature other than one on the face of the object may be used for axial alignment, if that feature is not subjected to wear.

FIG. 11 illustrates an example of a cross-sectional profile of a test object other than a cam, with which the method may be used. The axis of rotation when the object is placed into the test system of FIG. 6 is shown. As stated above, it should be understood that the method can be applied to evaluating pre-test versus post-test changes on a surface of any object having a non-concave cross-sectional profile. In FIG. 11, the object has a rectangular cross-sectional profile, with the method used to measure wear on one or more edges.

An advantage of the above-described method is that because a laser scan micrometer is a non-contact optical measurement apparatus, the spatial relation between the measured cam lobe and the laser scan micrometer measurement heads does not need to be as rigidly defined as with a profilometer.

Another advantage is that measurement with a laser scan micrometer is independent of run-out. In contrast, measurements using a contact stylus profilometer must account for error caused by run-out.

What is claimed is:

1. A method of comparing surface profiles of an object, the object being rotatable on an axis in angular increments, such that the object has a longitudinal dimension and an axial dimension, comprising:
    mounting the object on an axis;
    acquiring a pre-test longitudinal profile of the object by:
        using a laser scan micrometer to scan the object in a longitudinal direction, rotating the object about the axis, re-scanning the object, measuring the scan length thereby obtaining a longitudinal height value, and repeating the preceding steps for a number of incremental rotations thereby obtaining a longitudinal height profile;
    repeatedly and incrementally moving the object in an axial direction and acquiring additional longitudinal height profiles, thereby acquiring a pre-test set of longitudinal height profiles;
    acquiring a post-test set of longitudinal height profiles for the object in the same manner as the pre-test set of longitudinal profiles;
    axially and rotationally aligning one or more pre-test longitudinal height profiles with corresponding post-test longitudinal height profiles; and
    comparing the difference between the pre-test longitudinal height profiles and the post-test longitudinal height profiles.

2. The method of claim 1, wherein the object has a rounded cross-sectional profile.

3. The method of claim 1, wherein the object has a rectangular cross-sectional profile.

4. The method of claim 1, wherein the object is a cam mounted on its camshaft and the rotation step uses the camshaft as the axis of rotation.

5. The method of claim 1, wherein the aligning step is performed by scanning a non-changing feature on a test object for axial alignment.

6. The method of claim 5, wherein the feature is a face of the object.

7. The method of claim 5, wherein the object is a cam on camshaft and the feature is a face of the camshaft.

8. The method of claim 1, wherein the aligning step is performed by scanning two non-changing features on a surface of the test object that protrude in the axial direction.

9. A laser scan measurement system for acquiring surface profiles of an object, the object having a physical axis for rotating the object, such that the object has a longitudinal dimension and an axial dimension relative to the axis, comprising:
   a laser scan micrometer having scan range;
   a first stepper motor operable to rotate the object about the axis in incremental angular positions;
   a second stepper motor operable to reposition the object or the laser scan micrometer in incremental axial positions;
   a motor control unit operable to control the angular position and the axial position of the object by generating control signals to the first stepper motor and the second stepper motor;
   wherein the motor control unit and the laser scan micrometer are operable to acquire a set of longitudinal height profiles of the object by:
   scanning the object in a longitudinal direction, rotating the object about the axis, re-scanning the object, measuring the scan length thereby obtaining a longitudinal height value, and repeating the preceding steps for a number of incremental rotations thereby obtaining a longitudinal height profile;
   repeatedly and incrementally moving the object in an axial direction and acquiring additional longitudinal height profiles, thereby acquiring a set of longitudinal height profiles.

10. The system of claim 9, wherein the control unit is further programmed to store data representing a pore-test set of longitudinal profiles and a post-test set of longitudinal height profiles, and to axially and rotationally align one or more pre-test longitudinal height profiles with corresponding post-test longitudinal height profiles.

11. The system of claim 10, wherein the aligning is performed by scanning a non-changing feature on a test object for axial alignment.

12. The system of claim 10, wherein the aligning is performed, for axial alignment by scanning two non-changing features on a surface of the test object that protrude in the axial direction.

13. The method of claim 10, wherein the control unit is further programmed to compare the difference between the pre-test longitudinal height profiles and the post-test longitudinal height profiles.

14. The system of claim 10, wherein the incremental rotations are all within the same range, which is equal to or less than 180 degrees.

15. The system of claim 10, wherein the second stepper motor moves the object.

16. The system of claim 10, wherein the second stepper motor moves the laser scan micrometer.

17. The method of claim 8, wherein the object is a cam on camshaft and the features are a center boss and a dowel pin on the face of the camshaft.

18. The method of claim 1, wherein the incremental rotations are all within the same range, which is equal to or less than 180 degrees.

* * * * *